US00PP14088P39

(12) United States Plant Patent
Cain

(10) Patent No.: US PP14,088 P3
(45) Date of Patent: Aug. 26, 2003

(54) GRAPEVINE CV. 'SUGRANINETEEN'

(75) Inventor: David W. Cain, Bakersfield, CA (US)

(73) Assignee: Sun World International, Inc., Bakersfield, CA (US)

( * ) Notice: Subject to any disclaimer, the term of this patent is extended or adjusted under 35 U.S.C. 154(b) by 307 days.

(21) Appl. No.: 09/770,926

(22) Filed: Jan. 25, 2001

(65) Prior Publication Data

US 2002/0133855 P1 Sep. 19, 2002

(51) Int. Cl.[7] ..... A01H 5/00
(52) U.S. Cl. ..... Plt./205
(58) Field of Search ..... Plt./205

(56) References Cited

U.S. PATENT DOCUMENTS

PP9,865 P 4/1997 Ralli et al. ..... Plt./47.1

*Primary Examiner*—Bruce R. Campell
*Assistant Examiner*—Michelle Kizilkaya
(74) *Attorney, Agent, or Firm*—Knobbe, Martens, Olson and Bear

(57) ABSTRACT

A new and distinct grapevine variety characterized by late ripening berries that are crisp, juicy, and elliptical in shape. Moreover, the berries attain a large size without the need for exogenous application of gibberellic acid, and possess a naturally red, commercially acceptable coloration even when grown in deep shade.

1 Drawing Sheet

BACKGROUND AND SUMMARY OF THE INVENTION

This invention relates to the discovery and asexual propagation of a new variety of grapevine, *Vitis vinifera* cv. 'Sugranineteen.' The new variety was first hybridized by David W. Cain in Wasco, Kern County, Calif., the variety being originated by controlled hybridization and subsequent ovule culture of normally abortive seeds. The new variety is characterized by producing crisp, juicy, large, elliptical berries that attain a naturally red color even in deep shade. The berries ripen late and do not require exogenous gibberellic acid application to obtain acceptable commercial size.

The seed parent of the new 'Sugranineteen' variety is the 'Sun World Seedling 89345-090-144' and the pollen parent is the 'Sun World Seedling 89361-091-364'. 'Sugranineteen' resembles '89345-090-144' in color, shape, and firmness. It differs from '89345-090-144' by having larger berries, and containing smaller seed traces. 'Sugranineteen' resembles '89361-091-364' in color, and differs from '89361-091-364' by having larger berries that are ovate rather than spherical. The parent varieties were first crossed in May, 1993, with the date of first flowering being May, 1996. The new 'Sugranineteen' variety was first asexually propagated by David W. Cain in December, 1996 near Wasco, Kern County, Calif., using hardwood cuttings.

The new grapevine variety cv. 'Sugranineteen' is distinguished from other commonly grown red seedless grapes such as the 'Emperor' (unpatented), 'Crimson' (unpatented), 'Flame Seedless' (unpatented), and 'Ralli Seedless' (U.S. Plant Pat. No. 9,865) by possessing late ripening elliptical berries that are naturally red. The new grapevine variety cv. 'Sugranineteen' most nearly resembles the 'Emperor' variety. It is distinguished from the 'Emperor' variety by producing soft, abortive, vestigial seed traces as opposed to the hard, fully developed seeds found in the 'Emperor' variety. 'Sugranineteen' also ripens approximately one month earlier than the 'Emperor' variety.

The new 'Sugranineteen' variety resembles the 'Crimson' (unpatented) grapevine variety but differs from 'Crimson' by producing larger and softer berries which are more nearly oval in shape. Moreover, 'Sugranineteen' berries develop a commercially acceptable red color under deep shade conditions as compared to the 'Crimson' variety which colors with difficulty.

'Sugranineteen' variety produces more elliptical berries as compared to the oval berries produced by 'Ralli Seedless'. 'Sugranineteen' has the ability to ripen approximately 7 weeks later than 'Ralli Seedless'. It also differs from 'Ralli Seedless' in that the berries have a higher sugar level, and can obtain a dark red color under warm conditions.

The new 'Sugranineteen' variety is distinguished from the 'Flame Seedless' variety by having larger, more elliptical berries as compared to the rounder berries of the 'Flame Seedless' variety. It is also distinguished from the 'Flame Seedless' variety in that it ripens approximately eight weeks later.

The new 'Sugranineteen' variety has been shown to maintain its distinguishing characteristics through successive asexual propagations by, for example, cuttings.

BRIEF DESCRIPTION OF THE FIGURE

The accompanying drawing in FIG. 1 illustrates in full color a typical cluster of berries, a young shoot, and a mature leaf blade of the new grapevine.

DETAILED BOTANICAL DESCRIPTION OF THE INVENTION

Figure 1:
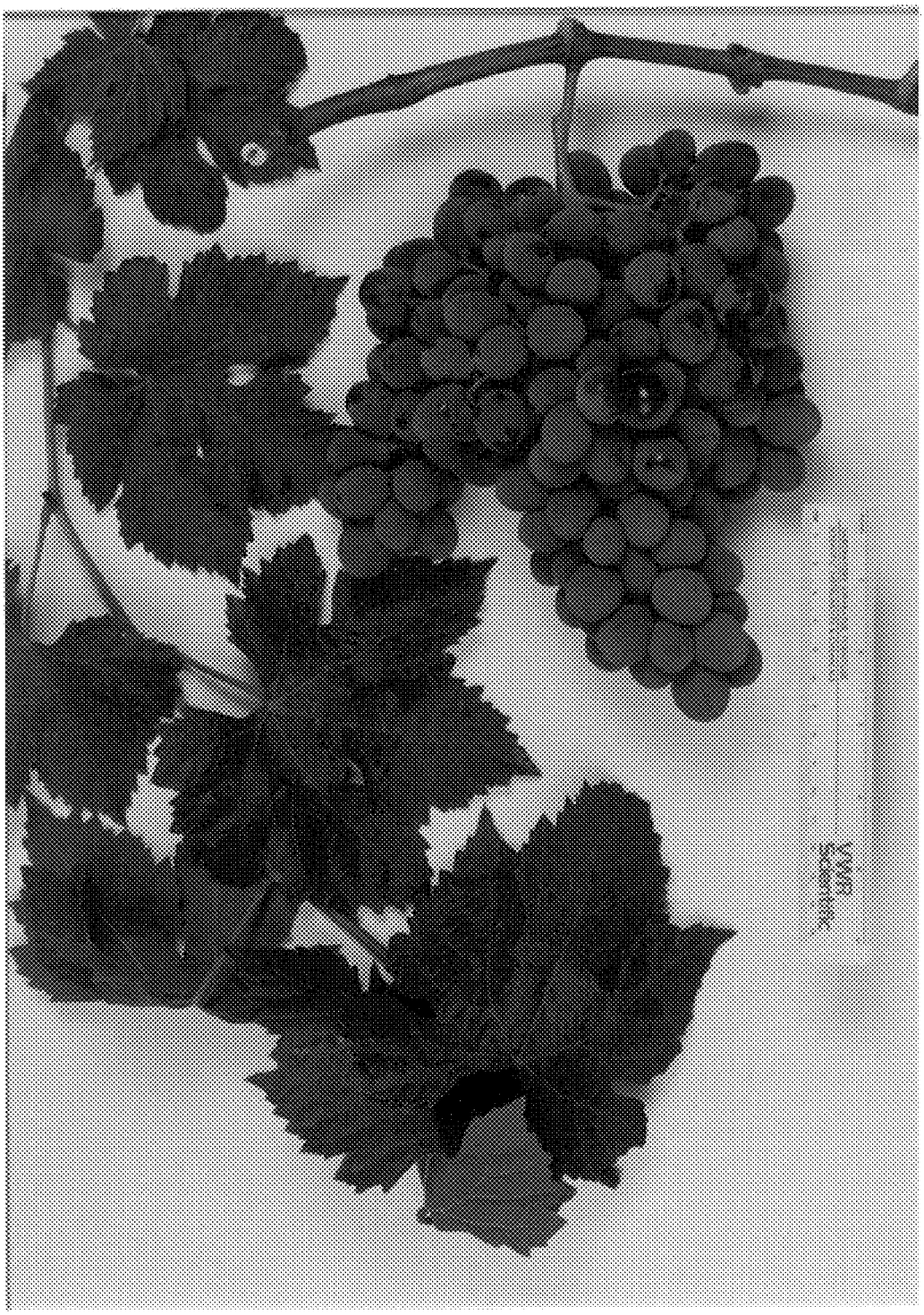

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

Many of the description values in this specification are based on and conform to those set forth by the International Board for Plant Genetic Resources Institute Grape Descriptors (Vitis spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugranineteen' plants grown in the vicinity of Wasco, Kern County, Calif., during 2000, and is believed to apply to plants of the variety grown under similar conditions of soil and climate elsewhere:

VINE

General:
- *Size.*—Medium to small.
- *Vigor.*—Medium to weak.
- *Density of foliage.*—Open.
- *Productivity.*—Very productive.
- *Root stock.*—Own root.

Trunk:
- *Shape.*—Slender.
- *Straps.*—Short-split.
- *Surface texture.*—Medium.
- *Inner bark color.*—About 177B.

SHOOTS

Young shoot:
- *Form of tip.*—Fully open.
- *Distribution of anthocyanin coloration of tip.*—Absent.
- *Intensity of anthocyanin coloration of tip.*—Absent.
- *Density of prostrate hairs on tip.*—Very sparse.
- *Density of erect hairs on tip.*—Absent.

Flowering shoot:
- *Vigor during flowering.*—Medium.
- *Attitude during flowering on shoots which are not tied.*—Semi-drooping.
- *Color of dorsal side of internodes.*—Green with extremely faint red on some; about 144A.
- *Color of ventral side of internodes.*—About green 144A.
- *Color of dorsal side of nodes.*—About green 144A.
- *Color of ventral side of nodes.*—About green 144A.
- *Density of erect hairs on nodes.*—None.
- *Erect hairs on internode.*—Absent.
- *Density of prostrate hairs on nodes.*—None.
- *Density of prostrate hairs on internodes.*—Absent.
- *Anthocyanin coloration of buds.*—Absent.

Tendrils:
- *Distribution on the shoot at full flowering.*—Discontinuous.
- *Thickness.*—Thick.
- *Color.*—About 144A.
- *Form.*—Trifurcated.
- *Number of consecutive tendrils.*—Up to two.
- *Length of tendril.*—Medium, about 29.2 cm.

LEAVES

Young leaves:
- *Color of upper surface of first 4 distal unfolded leaves.*—Copper.
- *Average intensity of anthocyanin coloration of six distal leaves prior to flowering.*—Weak.
- *Density of prostrate hairs between veins at lower surface of 4th distal unfolded leaf.*—Absent.
- *Density of erect hairs between veins at lower surface of 4th distal unfolded leaf.*—Absent.
- *Density of prostrate hairs on veins at lower surface of 4th distal unfolded leaf.*—Very sparse.
- *Density of erect hairs on veins at lower surface of 4th distal unfolded leaf.*—Absent.

Mature leaves:
- *Average length.*—About 16.2 cm.
- *Average width.*—About 20.6 cm.
- *Size of blade.*—Large.
- *Shape of blade.*—Pentagonal.
- *Number of lobes.*—5 to 7.
- *Anthocyanin coloration of main veins on the upper side of the blade.*—Absent.
- *Mature leaf profile.*—Undulate.
- *Blistering surface of blade upper surface.*—Medium.
- *Leaf blade tip.*—In the plane of the leaf.
- *Undulation of margin.*—Pronounced.
- *Apex.*—Cuspidate.
- *Thickness.*—Medium.
- *Undulation of blade between main and lateral veins.*—Only near petiole.
- *Shape of teeth.*—Both sides convex.
- *Length of teeth.*—Short.
- *Ratio length/width of teeth.*—Medium 9.3:14.3 mm.
- *General shape of petiole sinus.*—Half open.
- *Tooth at petiole sinus.*—Absent.
- *Petiole sinus limited by veins.*—Absent.
- *Shape of upper lateral sinus.*—Lobes slightly overlapping.
- *Depth of upper lateral sinus.*—Medium.
- *Density of prostrate hairs between veins on lower surface of blade.*—Absent.
- *Density of erect hairs between veins on lower surface of blade.*—Absent.
- *Density of prostrate hairs on main veins on lower surface of blade.*—None or very sparse.
- *Density of erect hairs on main veins on lower surface of blade.*—None or very sparse.
- *Density of prostrate hairs on main veins on upper surface of blade.*—Absent.
- *Autumn coloration of leaves.*—About yellow 11B.

Upper surface:
- *Color.*—About 147B.
- *Surface texture.*—Rugose.
- *Surface appearance.*—Semi-glossy.
- *Goffering of blade.*—Present.

Lower surface:
- *Color.*—About 147C.
- *Anthocyanin coloration of main veins on lower leaf surface.*—Absent to extremely weak.
- *Glossiness.*—Weak.
- *Pubescence.*—Absent.
- *Surface texture.*—Rugose.

Petiole:
- *Length of petiole.*—Long, about 14.7 cm.
- *Length of petiole compared to middle vein.*—Slightly shorter.
- *Density of prostrate hairs on petiole.*—None.
- *Density of erect hairs on petiole.*—None.
- *Growth of axillary shoots.*—Weak.
- *Shape of base of petiole sinus.*—V-shaped.

Woody shoot:
- *Shape.*—Slender.
- *Internode length.*—Short, about 112.3 mm.
- *Width at node.*—About 13.3 mm.

*Cross section.*—Circular.
*Surface.*—Striate.
*Main color.*—About yellowish brown 166D.
*Lenticels.*—Absent.
*Density of erect hairs on nodes.*—None.
*Density of erect hairs on internodes.*—None.
*Growth of axillary shoots.*—Weak.

Buds:
*Shape.*—Slightly pointed.
*Size.*—Medium; about 0.45 cm length by 0.58 cm width.
*Position.*—Slightly held out.
*Cane bud fruitfulness.*—Basal fruitful; seldom dead.
*Time of bud burst.*—Late.

FLOWERS

General:
*Flower sex.*—Hermaphrodite.
*Length of first inflorescence.*—Long.
*Position of first flowering node.*—$4^{th}$.
*Number of inflorescences per shoot.*—Up to 1.
*Date of full bloom.*—May 7, 2000.
*Time of bloom.*—Late.
*Size* (*diameter of fully open flower*).—Large.

FRUIT

General:
*Ripening period.*—Late, about 30 days after 'Thompson Seedless' variety.
*Use.*—Fresh market.
*Keeping quality.*—Good.
*Resistance.*—Insects: medium (typical of *Vitis vinifera*). Diseases: medium (typical of *Vitis vinifera*).
*Shipping quality.*—Good.
*Date of first harvest.*—Sep. 1, 2000.
*Solids-sugar.*—High, about 21%.
*Refractometer test.*—About 23.0° brix on Oct. 13, 2000.
*Acid.*—Low, about 4.2 g/L tartaric acid.
*Juice pH.*—About 4.08.

Cluster:
*Bunch size* (*peduncle excluded*).—Medium to large.
*Bunch length* (*peduncle excluded*).—Long, about 28.8 cm.
*Bunch width.*—About 16.8 cm.
*Bunch weight.*—High, averaging about 845 g.
*Bunch density.*—Medium.
*Number of berries.*—About 145.
*Form.*—Conical.

Peduncle:
*Length of peduncle.*—Short, about 3.8 cm.
*Lignification of peduncle.*—Medium.
*Color.*—About 145B.

Berry:
*Size.*—Medium to large.
*Uniformity of size.*—Uniform.
*Berry weight.*—Medium to high, about 5.6 g.
*Shape.*—Narrow elliptic to elliptic.
*Presence of seeds.*—Rudimentary.
*Cross section.*—Circular.
*Dimensions.*—Longitudinal axis about 24.3 mm; horizontal axis about 19.8 mm.
*Skin color* (*without bloom*).—About red-grey 187B.
*Coloration of flesh.*—Clear.
*Juiciness of flesh.*—Very juicy.
*Berry firmness.*—Firm.
*Particular flavor.*—None.
*Bloom* (*cuticular wax*).—Very strong.
*Pedicel length.*—About 9.5 mm.
*Berry separation from pedicel.*—Difficult.
*Visibility of hilum.*—Slightly clear.

Skin:
*Thickness.*—Thick.
*Texture.*—Tough.
*Reticulation.*—Absent.
*Roughness.*—Absent.
*Tenacity.*—Tenacious to flesh.
*Tendency to crack.*—None.

What is claimed is:

1. A new and distinct variety of grapevine cv. 'Sugranineteen' as herein illustrated and described.

* * * * *